United States Patent [19]

Slepian

[11] Patent Number: 5,328,471

[45] Date of Patent: Jul. 12, 1994

[54] METHOD AND APPARATUS FOR TREATMENT OF FOCAL DISEASE IN HOLLOW TUBULAR ORGANS AND OTHER TISSUE LUMENS

[75] Inventor: Marvin J. Slepian, Cleveland Heights, Ohio

[73] Assignee: Endoluminal Therapeutics, Inc., Tucson, Ariz.

[21] Appl. No.: 101,966

[22] Filed: Aug. 4, 1993

Related U.S. Application Data

[63] Continuation of Ser. No. 14,043, Feb. 5, 1993, abandoned, which is a continuation of Ser. No. 869,907, Apr. 15, 1992, abandoned, which is a continuation of Ser. No. 759,048, Sep. 5, 1991, abandoned, which is a continuation of Ser. No. 485,287, Feb. 26, 1990, abandoned.

[51] Int. Cl.$^5$ .................... A61M 25/00; A61M 29/00
[52] U.S. Cl. ................................ 604/101; 606/194; 128/898
[58] Field of Search .................. 604/95–103; 606/191, 194, 195; 128/898

[56] References Cited

U.S. PATENT DOCUMENTS

| | | |
|---|---|---|
| 2,642,874 | 6/1953 | Keeling . |
| 2,854,982 | 10/1958 | Pagano . |
| 3,868,956 | 3/1975 | Alfidi et al. . |
| 3,880,158 | 4/1974 | Gurney . |
| 3,987,000 | 10/1976 | Gleichenhagen et al. . |
| 4,140,126 | 2/1979 | Choudhury . |
| 4,156,067 | 5/1979 | Gould . |
| 4,272,518 | 6/1981 | Moro et al. . |
| 4,377,010 | 3/1983 | Fydelor et al. . |
| 4,423,725 | 1/1984 | Baran et al. ............... 604/101 |
| 4,445,892 | 5/1984 | Hussein et al. . |
| 4,448,188 | 5/1984 | Loeb . |
| 4,459,252 | 7/1984 | MacGregor . |
| 4,503,569 | 3/1985 | Dotter . |
| 4,520,823 | 6/1985 | LeVeen et al. . |
| 4,553,545 | 11/1985 | Maass et al. . |

(List continued on next page.)

FOREIGN PATENT DOCUMENTS

| | | |
|---|---|---|
| 0183372 | 6/1986 | European Pat. Off. . |
| 8912478 | 12/1989 | PCT Int'l Appl. ............ 604/104 |

OTHER PUBLICATIONS

Boretos, "Improved Intravascular Delivery of Drug Via a Polyethylene Jet Catheter," The 13th Annual Meeting of the Society of Biomaterials, p. 128.

Kerenvi, et al., "Local Enzymatic Treatment of Atherosclerotic Plaques," Experimental and Molecular Patholgy, vol. 49, pp. 330–338 (1988).

McBride, et al., "Restenosis After Successful Coronary Angioplasty," The New England Journal of Medicine, pp. 1734–1737 (1988).

Primary Examiner—Stephen C. Pellegrino
Assistant Examiner—William W. Lewis
Attorney, Agent, or Firm—Kilpatrick & Cody

[57] ABSTRACT

Diseased portions of tissue lumens can be advantageously treated by the focal introduction of at least one therapeutic agent to the lumen at the diseased point. This can be accomplished by (a) introducing a catheter into the tissue lumen, said catheter comprising first and second expansile members and means for supplying therapeutic agent into a space between said first and second expansile members, and said catheter being positioned such that said first and second expansile members are disposed on opposite sides of the diseased region;

(b) expanding the expansile members to occlude the diseased region of the tissue lumen;

(c) introducing therapeutic agent to the occluded diseased region via said means for supplying therapeutic agent;

(d) allowing the catheter to remain in place for a therapeutically effective period of time;

(e) contracting the expansile members; and (f) removing the catheter. A particularly preferred application of the method of the invention is "bloodless angioplasty," in which the occluded diseased region is washed to remove blood prior to the introduction of the therapeutic agent. Then, the diseased region is treated with a therapeutic agent to suppress cell proliferation in the diseased region. The plaque is then disrupted. Finally, the occluded region may be treated with a medicament to promote vessel healing and sealed with a polymeric coating.

13 Claims, 3 Drawing Sheets

U.S. PATENT DOCUMENTS

| | | |
|---|---|---|
| 4,573,966 | 3/1986 | Weikl et al. |
| 4,580,568 | 4/1986 | Glanturco |
| 4,610,662 | 9/1986 | Weikl et al. |
| 4,636,195 | 1/1987 | Wolinsky |
| 4,650,466 | 3/1987 | Luther |
| 4,655,746 | 4/1987 | Daniels et al. |
| 4,655,771 | 4/1987 | Wallsten |
| 4,674,506 | 6/1987 | Alcond |
| 4,690,684 | 9/1987 | McGreevy et al. |
| 4,701,509 | 10/1987 | Sun et al. |
| 4,702,917 | 10/1987 | Schindler |
| 4,733,665 | 3/1988 | Palmaz |
| 4,744,366 | 5/1988 | Jang |
| 4,754,752 | 7/1988 | Ginsburg et al. |
| 4,763,654 | 8/1988 | Jang |
| 4,771,777 | 9/1988 | Horzewski et al. |
| 4,781,677 | 11/1988 | Wilcox |
| 4,799,479 | 1/1989 | Spears |
| 4,820,298 | 4/1989 | Leveen et al. |
| 4,832,688 | 5/1989 | Sagae et al. |
| 5,100,429 | 3/1992 | Sinofsky et al. |
| 5,147,385 | 9/1992 | Beck et al. |

METHOD AND APPARATUS FOR TREATMENT OF FOCAL DISEASE IN HOLLOW TUBULAR ORGANS AND OTHER TISSUE LUMENS

This is a continuation of application Ser. No. 08/014,043 filed on Feb. 5, 1993, now abandoned, which is a continuation of Ser. No. 07/865,907 filed Apr. 15, 1992, now abandoned, which is a continuation of Ser. No. 07/759,048, now abandoned, filed Sep. 5, 1991, which is a continuation of Ser. No. 07/485,287, filed Feb. 26, 1990, now abandoned.

BACKGROUND OF THE INVENTION

This application relates to the localized treatment of disease in hollow tubular organs, such as blood vessels, and other tissue lumens. The treatment regime involves the introduction of a therapeutic agent into a region of the tissue lumen defined by two expansile members. In particular, the application relates to the use of this technique to perform "bloodless angioplasty" in blood vessels having flow restrictions due to atherosclerotic plaque.

Within the bodies of animals, including man, there exist those organs or structures having hollow or tubular geometry, for example blood vessels such as arteries or veins, the gut and the bladder. In addition, there exist many "solid" organs which possess true spaces such as cavities, cavernous sinuses, lumens etc. These "solid" organs include the heart, liver, kidney and pancreas. Finally disease processes (e.g., necrotic tumors) and traumatic injury may create spaces within otherwise solid organs.

The lumens afforded by these various types of spaces can be affected by a variety of disease processes. For example, the lumen may be occluded thus limiting or preventing flow through the lumen. Since the lumen of many hollow organs serves a vital function, e.g., the transit conduit for blood, urine, bile or food, this restriction of flow through the lumen is detrimental. A particular example is the development and growth of an occluding atheroma (atherosclerotic plaque) in an artery, thereby reducing the blood flow through the artery.

In many cases, the wall of a tissue lumen has a significant barrier function as well as acting as a conduit for fluids. As an example, in a blood vessel, the "intima" or endothelial lining layer separates overflowing blood from the underlying middle or "media" portion of the vessel. Since the media is highly thrombogenic this separation is necessary to avoid clotting of the blood in normal blood vessels. Further, the media, if exposed to overflowing blood as a result of violation of the intimal barrier may be stimulated by platelets and macrophages in the blood, leading to smooth muscle cell proliferation and a regeneration of the stenosis. Disease conditions, such as advanced ulcerated atherosclerotic lesions, and in some instances intervention techniques, can disrupt this barrier layer leading to local blood clotting, inflammation and diffusion of growth stimulating factors such as platelet derived growth factor (PDGF), interleukin-1, and macrophage-derived growth factor (MDGF) into the media with subsequent activation, migration and proliferation of smooth muscle cells in the intima leading to a local buildup and regrowth of the stenosis.

Disease processes can also lead to the alteration of the structure and/or function or the tissue surrounding the lumen. For example, part of the tissue wall may be replaced by a cancerous/tumorous region or by an inflammatory zone. In advanced atherosclerosis, the vessel wall is replaced with lipid and inflammatory cell infiltrates, newly proliferated smooth muscle cells, fibrotic collagen and other connective tissue and dense calcium deposits. This replacement dramatically alters vessel function preventing (1) vessel vasomotion, i.e., the ability dilate or contract thereby altering blood flow based on organ metabolic demands; (2) normal flux in cellular nutrients into and through the vessel, i.e., glucose and oxygen as well as outflow of metabolic breakdown products/wastes; (3) normal release of downstream acting vasoreactive substances, i.e., endothelial derived relaxation factor (EDRF); and (4) normal metabolism of locally acting growth substances such as PDGF made by endothelial cells, thereby altering local vessel wall growth control and repair capabilities.

Further, even if there is not a change in the apparent makeup of the tissue surrounding the lumen, the metabolism of these cells may change. Thus, the production of required mediators such as growth factors and hormones may be disturbed. This also happens in atherosclerosis, where trans-vessel wall flow of nutrients, oxygen, lipid compounds, and growth factors are typically altered.

Although the types of problems which can occur in hollow organs and tissue lumens are generally recognized, the treatment regimes available generally attempt to treat the symptom rather than the underlying cause. This has a number of drawbacks, as can be illustrated using atherosclerosis as an example.

In atherosclerosis, the overall problem is the progressive build-up of an atheroma or atherosclerotic plaque at a focal location on an artery wall. The plaque is a complex of multi-component three dimensional structure composed of proliferating smooth muscle cells, stimulated macrophages and other inflammatory cells, chemically modified lipid components, i.e., cholesterol, oleate:linoleate esters, stiff connective tissue, i.e., collagen, and calcium. The distribution of plaque in the vessel wall is such that the bulk of the disease mass resides as an obstructing growth or "bulge" within the vessel lumen. This leads to reduced blood flow across the point of the plaque and subsequent reduced downstream blood flow. If such a restriction of flow occurs in the vital arterial beds, e.g., the coronary arteries in the heart or the carotid artery in the neck, the reduction of blood flow can lead to angina in the heart or a transient ischemic attack (TIA) in the brain. Complete flow cut-off will lead to heart attack or stroke, respectively.

Treatment for atherosclerosis has progressed from coronary artery bypass grafting (CABG) to catheter based techniques such as percutaneous transluminal coronary angioplasty. (PTCA) Thus, the state of the art has gone from merely by-passing the problem region to actually attempting to relieve the effects of the obstruction by direct attack and dilatation of the lesion. These attempts have led to the development of various catheter designs and treatment techniques. For example, U.S. Pat. No. 4,636,195 to Wolinsky describes the use of a catheter with two occluding balloons and a conduit for supplying a solubilizing agent to dissolve the plaque. A central balloon is included to force the solubilizing agent into the plaque. U.S. Pat. No. 4,610,662 of Weikl et al. describes a catheter which isolates the diseased region using a catheter having two expandable balloons and then introduces a chemical, such as digestive enzymes, for dissolving the plaque between the balloons.

A similar approach to the treatment of gall stones is disclosed in U.S. Pat. No. 4,781,677 to Wilcox.

These approaches, however, like the basic technique of angioplasty itself, make no attempt to address the underlying pathophysiology that is operant or to otherwise biomanipulate the lesion. Thus, there is no effort to induce lesion regression or resorption or the full disappearance of the lesion with healing and replacement of the diseased wall segment with a healthy wall segment with normal vessel components and function. The present invention fills this need, by providing for the focal administration of therapeutic agents to a diseased region, either alone or in conjunction with a physical attack (such as PTCA) on the diseased region.

SUMMARY OF THE INVENTION

In accordance with the claimed invention, diseased portions of tissue lumens can be advantageously treated by the focal introduction of at least one therapeutic agent to the lumen at the diseased point. This can be accomplished by (a) introducing a catheter into the tissue lumen, said catheter comprising first and second expansile members and means for supplying therapeutic agent into a space between said first and second expansile members, and said catheter being positioned such that said first and second expansile members are disposed on opposite sides of the diseased region;

(b) expanding the expansile members to occlude the diseased region of the tissue lumen;

(c) introducing therapeutic agent to the occluded diseased region via said means for supplying therapeutic agent;

(d) allowing the catheter to remain in place for a therapeutically effective period of time;

(e) contracting the expansile members; and (f) removing the catheter.

A particularly preferred application of the method of the invention is "bloodless angioplasty." In this application, the occluded diseased region is washed to remove blood prior to the introduction of the therapeutic agent. Then, the diseased region is treated with a therapeutic agent to suppress cell proliferation in the diseased region. The plaque is then disrupted, for example by conventional balloon angioplasty, atherectomy, laser plaque removal or ablation. Finally, the occluded region may be treated with a medicament to promote vessel healing and sealed with a polymeric coating. Because blood does not come into contact with the media which may be exposed during the disruption of the lesion, the risks of clotting in this technique are reduced. Further, the "wounded," stimulated and exposed media smooth muscle cells are not exposed during the immediate post-dilatation time when they are most sensitive to activation and stimulation by various factors found in the blood, the predominant mechanism leading to restenosis and long term PTCA failure. Thus, the anti-proliferative therapy will further reduce the likelihood of long term restenosis, through inhibition of smooth muscle cell proliferation which is maximum during the first 12 to 24 hours following treatment.

The method of the invention is advantageously practiced using a specially adapted catheter comprising at least two expansile members, a reservoir containing the therapeutic agent and a least one conduit for supplying therapeutic agent to the between the two expansile members.

DETAILED DESCRIPTION OF THE INVENTION

Figure 1A:
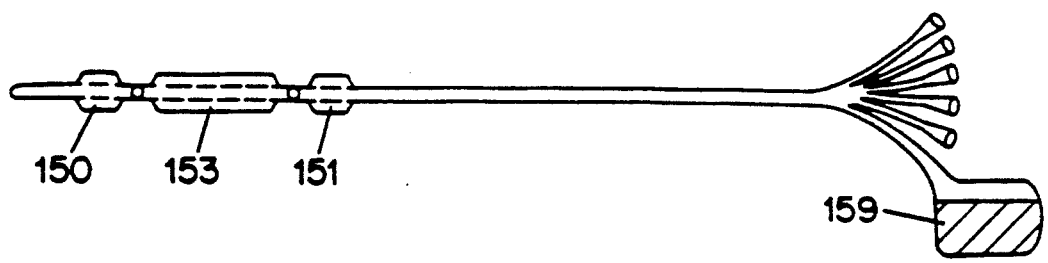
FIGS. 1a and 1b show two views of a catheter device in accordance with the invention.

As used in the specification and claims of this application, the term "therapeutic agent" refers to substances which alter the metabolism of the cells or reduce the tendency for thrombosis within the diseased portions of the tissue. Examples for use in coronary artery applications are vasodilating agents i.e. nitrates and calcium channel blocking drugs; anti-proliferative agents i.e. colchicine and alkylating agents; intercalating agents; growth modulating factors such as interleukins, transformation growth factor b, congeners of platelet derived growth factor and monoclonal antibodies directed against growth factors; anti-thrombotic agents, e.g., anti-GIIb/3a, trigramin, prostacyclin and salicylates; thrombolytic agents e.g. streptokinase, urokinase, tissue plasminogen activator (TPA) and anisoylated plasminogen-streptokinase activator complex (APSAC); anti-inflammatory agents, both steriodal and non-steroidal and other agents which may modulate vessel tone, function, arteriosclerosis, and the healing response to vessel or organ injury post intervention. Anti-proliferative drugs or high efficacy anti-inflammatory drugs are also useful for treatment of focal vasculitides or other inflammatory arteritidies, e.g., granulomatous arteritis, polyarteritis nodosa, temporal arteritis and Wegner's granulomatosis. Anti-inflammatory agents are also useful in connection with indications such as inflammatory bowel disease, Crohn's disease, ulcerative colitis and focal GI inflammatory diseases. In other applications, adhesives may be introduced in accordance with the invention to help heal dissections, flaps and aneurysms. Exemplary adhesives include cyanoacrylates, gelatin/resorcinal/formol, mussel adhesive protein and autologous fibrinogen adhesive. The term "therapeutic agents" does not encompass solubilizing or dissolving agents which disrupt the atherosclerotic plaque.

Catheter devices in accordance with the invention may include a variety of variations and modifications as will be discussed in greater detail below. In general, however, the catheters bodies for use in this invention can be made of any known material, including metals, e.g. steel, and thermoplastic polymers, and may be continuous tubes or woven, spring-like structures. The expansile members balloons may be made from compliant materials such as latex or silicone, or non-compliant materials such as polyethyleneterephthalate (PET), polyvinylchloride (PVC), polyethylene or nylon. The catheter may also include markers in one or more locations to aid in locating the catheter. These markers can be, for example, fluoroscopic radio-opaque bands affixed to the tubular body by heat sealing.

As used in the specification and claims of this application, the term "paving" refers to the application of a conforming polymeric coating to the surface of the tissue lumen. Thus, in "paving," a polymeric material, either in the form of a monomer or prepolymer solution or as an at least partially pre-formed polymeric product, is introduced into the lumen of the blood vessel and positioned at the point of the original stenosis. The polymeric product is then reconfigured to conform to and maintain intimate contact with the interior surface of the blood vessel such that a paving and sealing coating is achieved. The polymeric paving and sealing material may incorporate therapeutic agents such as drugs, drug producing cells, cell regeneration factors or even progenitor cells of the same type as the involved organ or histologically different to accelerate healing processes. Paving is described further in U.S. Patent application No. 07/235,998 and International Patent Application No. PCT/US89/03593, both of which are incorporated herein by reference.

Figure 1B:
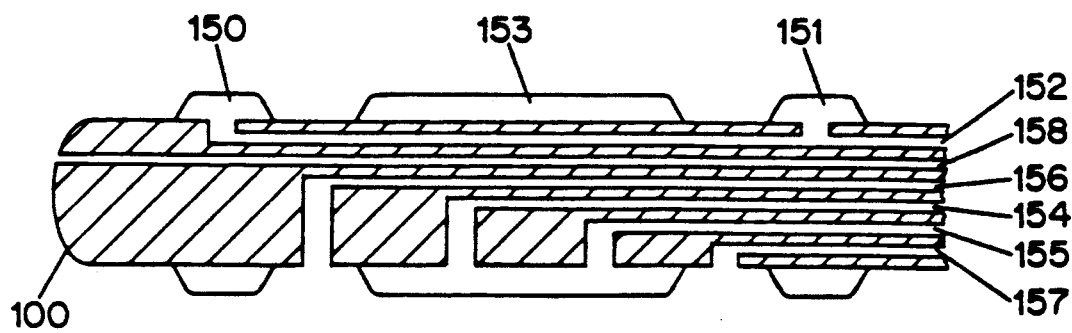
Figure 2:
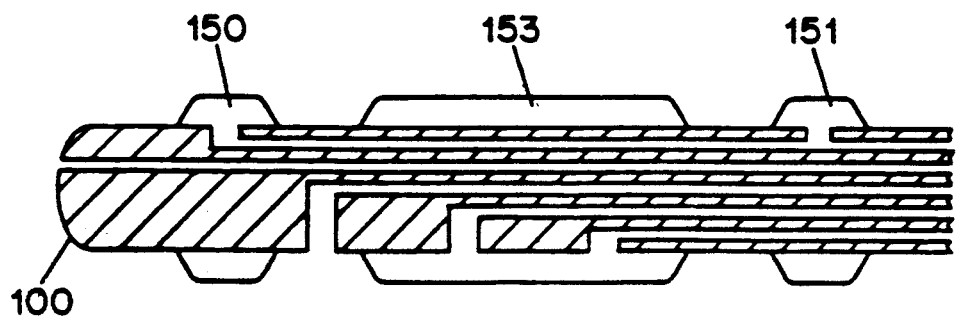
FIG. 2 shows a catheter device in accordance with the invention.

FIG. 1 shows a six lumen catheter device in accordance with the invention. In FIG. 1, there are two expansile members 150 and 151, both connected to conduit 152. Expansile members 150 and 151 serve to fix the position of the tubular body 100 within a tissue lumen and isolate the diseased portion of the tissue lumen between them where the therapeutic agent will be applied. Expansile member 153 may be a standard angioplasty balloon or used in deployment of a polymer paving, or both, and is provided with circulating flow via conduits 154 and 155. In the case that expansile member 153 is used to deploy a polymeric paving, conduits 154 and 155 can be used to provide temperature control to the isolated portion of the tissue lumen, as well as acting to configure the polymeric coating formed by expanding a polymeric sleeve and other deployed form fitted over expansile member 153. The therapeutic agent is provided from reservoir 159 through conduit 156, with conduit 157 acting as a drain line (or vice versa) to allow flow of fluid through the isolated portion of the tissue lumen ("superfusion"). The drain line is not required, however, and a simple infusion catheter could omit one of the conduits 156 or 157 as in the five lumen designs of FIG. 2 although a perfusion design is preferred. The sixth conduit 158 is also optional, but can be advantageously used for guide wires, diagnostic or therapeutic device passage, or distal fluid perfusion. If conduit 158 has an aperture proximal to balloon 151, it can be used as a by-pass conduit for passive perfusion during occlusion.

The catheter of FIG. 1 can be used in accordance with the method of the invention to perform procedures such as "bloodless angioplasty" as shown schematically in FIG. 3. In this technique, a catheter 1 is inserted into a partially blocked blood vessel 2 into the region of the lesion 3. (FIG. 3a) The catheter is positioned such that expansile members 150, 151 are disposed on opposite sides of the lesion 3 and expansile members 150, 151 are then expanded to isolate a zone 4 around the lesion 3. The isolated zone 4 is then washed to remove the blood from the region to be treated. This is done by supplying saline or other biocompatible material while removing blood. (FIG. 3b) After the blood is washed from the isolated zone 4, a therapeutic agent such as an antiproliferative agent is introduced from the reservoir of the catheter. (FIG. 3c) Suitable agents include agents for interfering with nucleic acid synthesis (e.g., Actinomycin D) or with cell division (e.g. cytochalsin B). Then, after a sufficient period of time has elapsed to allow the therapeutic agent to be effective, the angioplasty balloon 153 is inflated to disrupt the lesion 3 in accordance with known balloon angioplasty procedure. (FIG. 3d) Additional or different therapeutic agent may be added at this point. The angioplasty balloon 153 in then contracted. (FIG. 3e) At this stage, a further therapeutic agent or a polymeric coating, with or without admixed antithrombotic or antiproliferative drug, is preferably applied to the area of the disrupted lesion to facilitate healing. The polymeric coating will also provide a barrier over exposed portions of the media. Finally, the expansile members 150 and 151 are contracted and the catheter is removed restoring normal blood flow. (FIG. 3f)

In the treatment of restenosis, the preferred therapeutic agent is an anti-proliferative drug. Useful anti-proliferative drugs are varied in structure and mode of action, and many may be generally viewed as unsuited for therapy during coronary operations under other circumstances. For example, chemotherapeutic agents which would have significant toxic side effects if administered through conventional routes (i.e., enteral (oral) or parenteral (intramuscular, IV or subcutaneous)) can be used with the claimed invention. These chemotherapeutic agents include actinomycin D, adriamycin, methotrexate, vinca alkaloids such as colchicine, cytochalsin, vincristine and vinblastine, 5-fluorouracil, and nitrogen mustard.

Other anti-proliferative drugs may also be used including heparins, in both anti-coagulant and non-anticoagulant form; anti-proliferative vasodilatory drugs, such as adenosine, cyclic GMP-elevating vasodilators, angiotensin converting enzyme inhibitors, calcium channel blockers and prostaglandin El; prostacyclin; trapidil, terbinafine, protein kinase C activating phorbol esters and dimethyl-sulfoxide (DMSO). Fish oil may also be used as an anti-proliferative agent and to inhibit endothelial production of platelet derived growth factor (PDGF). Fish oil could not be administered in a conventional IV mode because of its insolubility, but could be used in accordance with the invention. Suramin, a PDGF antagonist with high anti-proliferative profiles but high clinical toxicities might also be employed.

Anti-proliferative antibodies to PDGF; or IL-1; TGFb; alpha and gamma interferon; angiopeptin (BIM 23034) and other peptides can also be used in the invention, although they cannot be administered generally because of the risk of an immune response.

Focal treatment with anti-coagulants is also desirable in restenosis treatment to reduce the tendency for clot formation at the PTCA site. These materials could be introduced in solution and allowed to soak into the vessel wall, or might be deposited as a gel or surfactant coating which adheres to the vessel wall.

As an alternative to the angioplasty balloon as shown in FIG. 1, plaque disruption can be carried out using a heated balloon to fuse disrupted tissue, as disclosed in U.S. Pat. No. 4,799,479 to Spears or U.S. Pat. No. 4,754,752 to Ginsburg et al.; a woven fibrous tube as disclosed in U.S. Pat. No. 4,650,466 to Luther; or laser light, as disclosed in U.S. Pat. No. 4,445,892 to Hussein et al., U.S. Pat. No. 4,448,188 to Loeb or U.S. Pat. No. 4,627,436 to Leckrone. Solubilizing agents may also be employed as disclosed by Weikl et al., Wilcox and Wolinsky.

The therapeutic agent used in accordance with the invention may be introduced in the form of a solution as described above. Alternatively, however, the therapeutic agent may be administered as a gas or in the form of microparticles. For example, as a gas, ethylene oxide, mustard gas or chloroform vapors may be administered in limited doses as antiproliferatives. Microparticles may be formed from the therapeutic agent in combination with biodegradable polymers such as polylactic acid, polyglycolic acid, polycaprolactone, polydioxanone, starch, gelatin and polyanhydrides or nondegradable polymers such as styrene or acrolein. Drug-containing liposomes may also be employed. Preferred sizes of microparticles are less than 4 microns, more preferably less than 1 micron (i.e. nanoparticles).

Figure 4:
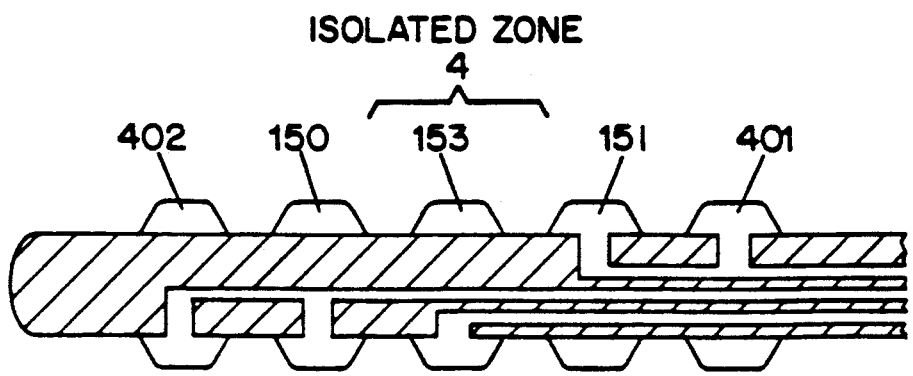
FIG. 4 shows a catheter device in accordance with the invention.
Figure 3A:
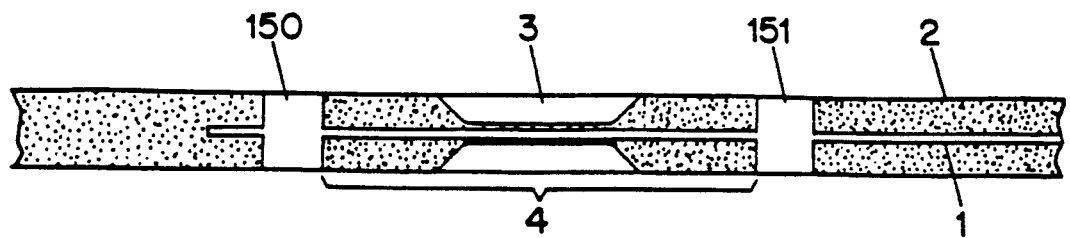
FIGS. 3a-3f show the steps for performing "bloodless angioplasty" in accordance with the invention.
Figure 3B:
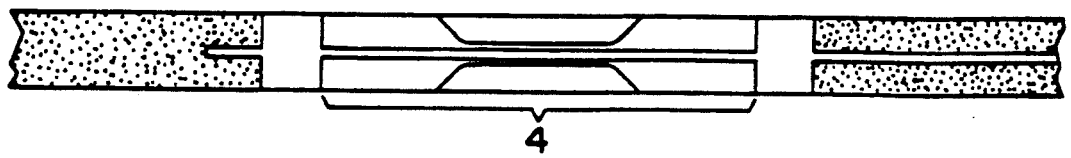
Figure 3C:
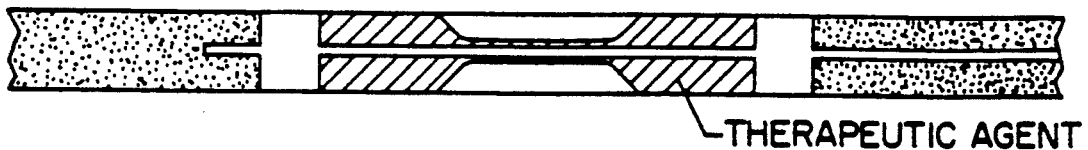
Figure 3D:
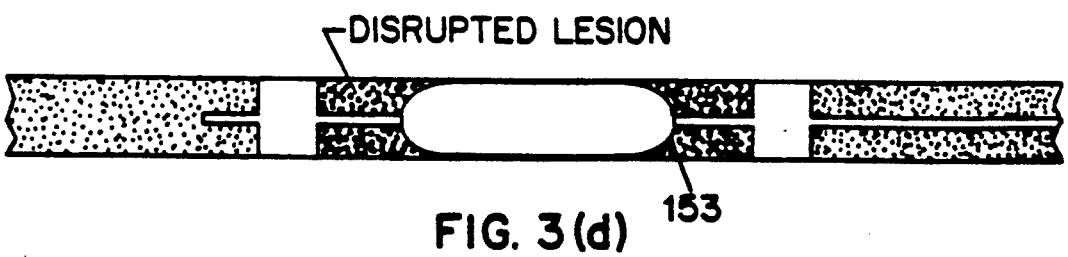
Figure 3E:
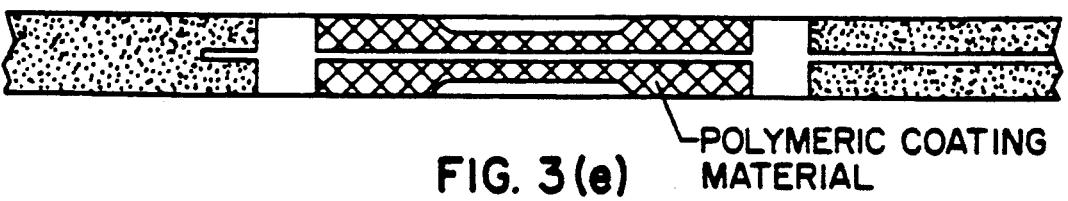
Figure 3F:
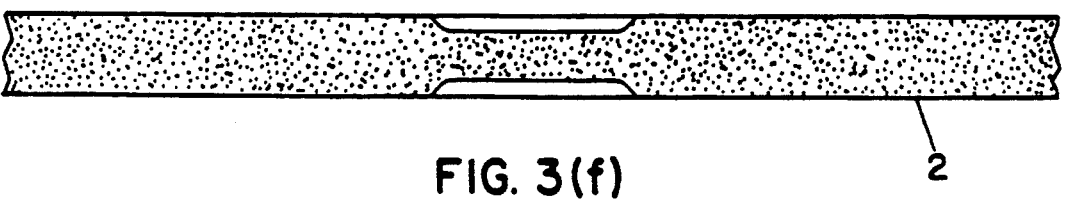

FIG. 4 shows a further catheter which may be used in accordance with the invention. In this catheter, back-up expansile members 401 and 402 are disposed outwardly from the principal occluding expansile members 150 and 151. This back-up expansile members create a safety zone to prevent spill-over of therapeutic agents from the isolated zone 4 into the blood stream.

Various other modifications to the basic design of the catheter shown in FIG. 1 are also contemplated within the scope of the invention. For example, a "weeping" balloon may be employed in place of the standard angioplasty balloon such that materials may be delivered to the isolated zone through pores in the balloon. Similarly, guidewires may be incorporated in the catheter of the invention, or the two occluding balloons may be disposed on slidably interlocking catheter portions to provide for adjustable interballoon distances. Finally, one or both of the balloons may be equipped with spray ports or nozzles to deliver a gas or particulate therapeutic agent to the isolated zone.

The catheter device of the invention may also include a pump or vacuum system to deliver the therapeutic agent from the reservoir to the tissue lumen. Such a pump may be servo-controlled to allow for dynamic pressurization of the isolated zone to facilitate diffusion and/or active penetration of the lesion. Alternate cycling of pressure and vacuum may be advantageously employed to facilitate penetration of the lesion or organ wall.

Other features that may also be included within the catheter of the invention include heating elements, such as coaxial heating elements within one or more sublumens of the catheter body to provide heat to the conduit to facilitate instillation of polymers or surfactants which are solid at room temperature but which melt with slight heating. Such heating elements are particularly applicable in the case where a polymeric coating is being formed, either during the introduction of therapeutic agent or as part of a post-disruption treatment. The catheter may also incorporate a high-frequency ultrasound crystal or element or other acoustically vibrating element between the two expansile members to facilitate fluid penetration into the lesion. Such devices may also facilitate vibrational or ultrasonic welding (i.e., coalescing) or polymer solutions or microparticles leading to the formation of coating on the vessel surface.

Figure 5:
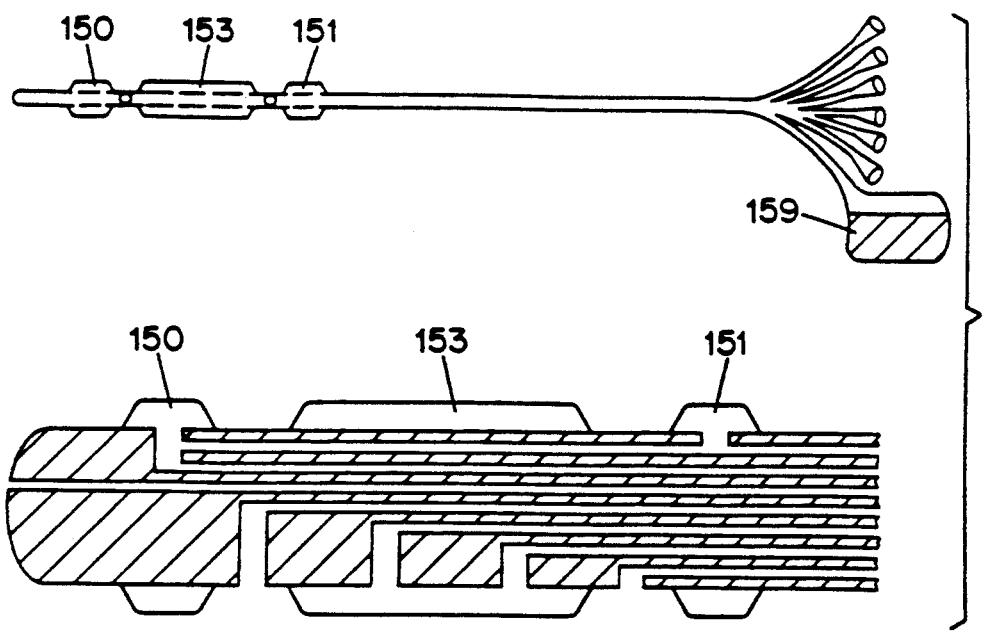
FIG. 5 shows two views of a catheter device in accordance with the invention.
Figure 6:
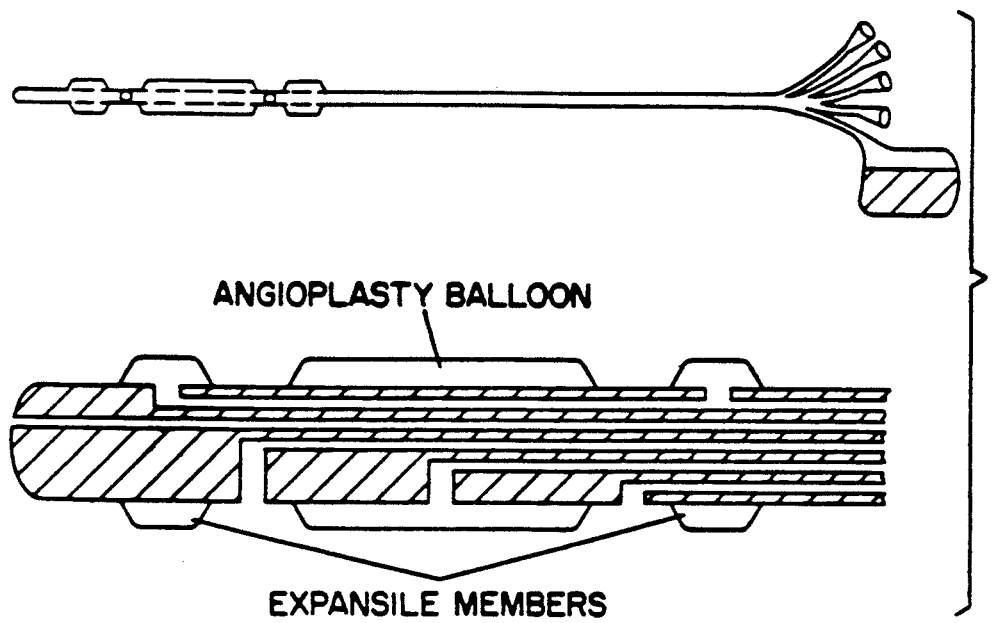
FIG. 6 shows two views of a catheter device in accordance with the invention.

In addition, the person skilled in the art will understand that variations in the number of lumens within the catheter body may be made without departing from the present invention. For example, FIG. 5 shows a seven lumen catheter in which the expansile members which occlude the diseased region are separately controlled through lumens 50 and 51. FIG. 6 shows a five lumen superfusion catheter, in which the expansion of the angioplasty balloon is controlled by a single lumen.

Figure 7:
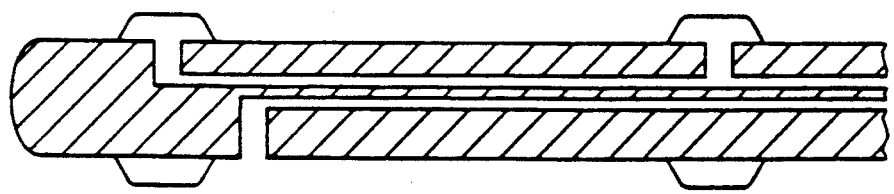
FIG. 7 shows a catheter device in accordance with the invention.

While the present invention is ideally suited to the practice of bloodless angioplasty, it not limited to this application. Indeed, the introduction of a therapeutic agent focally at the situs of disease using a dual balloon catheter is useful for a wide variety of indications. In this case, the angioplasty balloon or other disruptive means may be omitted from between the two occluding balloons, and the catheter may be simply a two lumen dual balloon catheter such as that shown in FIG. 7 connected to a reservoir containing the therapeutic agent. Such a catheter could be used to deliver focal therapy in instances of bladder tumors, GI polyps, liver tumors, bronchial tumors, renal tumors and uterine tumors. In addition, treatment of inflammatory bowel disease, Crohn's disease, ulcerative colitis and focal GI inflammatory diseases where the application of anti-inflammatory or wound healing composition may prove valuable.

I claim:

1. A method for providing localized therapy with a therapeutic agent to a diseased region in a tissue lumen, comprising:
   (a) introducing a catheter into the tissue lumen, said catheter comprising first and second expansile members and means for supplying the therapeutic agent into a space between said first and second expansile members and said catheter being positioned such that said first and second expansile members are disposed on opposite sides of the diseased;
   (b) expanding the expansile members to occlude the diseased region of the tissue lumen;
   (c) washing the occluded region to remove body fluid;
   (d) introducing therapeutic agent to the washed occluded diseased region via said means for supplying therapeutic agent;
   (e) disrupting the diseased region of the tissue lumen to loosen diseased tissue after introduction of the therapeutic agent;
   (f) allowing the catheter to remain in place for a therapeutically effective period of time;
   (g) contracting the exapansible member; and
   (h) removing the catheter.

2. A method according to claim 1, wherein the tissue lumen is the interior of a blood vessel.

3. A method according to claim 2, wherein the therapeutic agent is selected from the group consisting of anti-thrombotic agents, thrombolytic agents, vasodilating agents, calcium channel blocking drugs, anti-proliferative agents, intercalating agents, growth modulating factors and anti-inflammatory agents.

4. A method according to claim 1, further comprising the step of paving the occluded region of the tissue lumen after disruption of the diseased region.

5. A method according to claim 4, wherein the paving is introduced as a liquid or gel.

6. A method according to claim 4, wherein the paving is introduced as an at least partially polymerized, deformable sleeve.

7. A method according to claim 1, wherein the disruption is performed with an angioplasty balloon.

8. A method for providing localized therapy with a therapeutic agent to a diseased region in a tissue lumen comprising the steps of:
  (a) introducing a catheter into the tissue lumen, said catheter comprising first and second expansile members and means for supplying therapeutic agent into a space between said first and second expansile members and said catheter being positioned such that said first and second expansile members are disposed on opposite sides of the diseased region;
  (b) expanding the expansile members to occlude the diseased region of the tissue lumen;
  (c) introducing therapeutic agent to the occluded diseased region via said means for supplying therapeutic agent;
  (d) paving the occluded region of the tissue lumen;
  (e) allowing the catheter to remain in place for a therapeutically effective period of time;
  (f) contracting the expansile members; and
  (g) removing the catheter.

9. A method according to claim 4, wherein the paving is introduced as a liquid or gel.

10. A method according to claim 4, wherein the paving is introduced as an at least partially polymerized, deformable sleeve.

11. A method for providing localized therapy to a diseased region in a tissue lumen, comprising:
  (a) introducing a catheter into the tissue lumen, said catheter comprising first and second expansile members and means for supplying the therapeutic agent into a space between said first and second expansile members and said catheter being positioned such that said first and second expansile members are disposed on opposite sides of the diseased;
  (b) expanding the expansile members to occlude the diseased region of the tissue lumen;
  (c) washing the occluded region to remove the body fluid contacting the occluded diseased region;
  (d) disrupting the diseased region of the tissue lumen to loosen diseased tissue;
  (e) allowing the catheter to remain in place for a therapeutically effective period of time;
  (f) contracting the exapansible member; and
  (i) removing the catheter.

12. The method of claim 11 further comprising administering a therapeutic agent to the occluded region.

13. The method of claim 12 wherein the therapeutic agent is a polymeric material.

* * * * *